United States Patent
Savage et al.

(10) Patent No.: US 9,888,942 B1
(45) Date of Patent: Feb. 13, 2018

(54) ADAPTOR FOR ROBOTICS CANNULA AND SEAL ASSEMBLY

(71) Applicant: Ethicon Endo-Surgery, Inc., Cincinnati, OH (US)

(72) Inventors: Jeffrey L. Savage, West Chester, OH (US); Omar J. Vakharia, Cincinnati, OH (US); William D. Dannaher, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 208 days.

(21) Appl. No.: 14/576,431

(22) Filed: Dec. 19, 2014

(51) Int. Cl.
*A61M 5/178* (2006.01)
*A61B 17/34* (2006.01)

(52) U.S. Cl.
CPC ...... *A61B 17/3462* (2013.01); *A61B 17/3421* (2013.01); *A61B 2017/3441* (2013.01); *A61B 2017/3464* (2013.01)

(58) Field of Classification Search
CPC .... A61M 39/26; A61B 17/34; A61B 17/3462; A61B 17/3474; A61B 17/3496; A61B 17/3498; A61B 2017/0042; A61B 2017/00477
See application file for complete search history.

(56) References Cited

U.S. PATENT DOCUMENTS

| | | | |
|---|---|---|---|
| 5,385,553 A | 1/1995 | Hart et al. | |
| 5,385,572 A | 1/1995 | Nobles et al. | |
| 5,449,370 A | 9/1995 | Vaitekunas et al. | |
| 5,609,604 A | 3/1997 | Schwemberger et al. | |
| 5,628,732 A | 5/1997 | Antoon et al. | |
| 5,697,913 A | 12/1997 | Sierocuk et al. | |
| 5,709,671 A | 1/1998 | Stephens et al. | |
| 5,792,135 A | 8/1998 | Madhani et al. | |
| 5,817,061 A | 10/1998 | Goodwin et al. | |
| 5,817,084 A | 10/1998 | Jensen | |
| 5,878,193 A | 3/1999 | Wang et al. | |
| 6,123,689 A | 9/2000 | To et al. | |

(Continued)

FOREIGN PATENT DOCUMENTS

DE    10 2009 032188 A1    1/2011

OTHER PUBLICATIONS

U.S. Appl. No. 61/597,603, filed Feb. 10, 2012.
International Search Report and Written Opinion dated Mar. 18, 2016 for Application No. PCT/US2015/065493, 14 pgs.

*Primary Examiner* — Rebecca E Eisenberg
(74) *Attorney, Agent, or Firm* — Frost Brown Todd LLC

(57) ABSTRACT

An adaptor apparatus comprises a seal assembly housing, a channel, and tapered surfaces. The adaptor apparatus is configured to connect a trocar seal assembly with a robotic trocar cannula and maintain pneumostasis in an insufflated body cavity of a patient. The seal assembly housing comprises an open area sufficient to receive, support, and fix the trocar seal assembly within the adaptor apparatus. The channel provides a pathway for inserting instruments from the trocar seal assembly and into the cannula. The robotic trocar cannula includes an annular flange and a tapered proximal opening. The tapered surfaces of the adaptor apparatus are configured to engage the annular flange and the tapered proximal opening of the cannula. The tapered surfaces of the adaptor apparatus are configured to complement the exterior of the annular flange and the angled opening of the cannula.

19 Claims, 14 Drawing Sheets

(56) References Cited

U.S. PATENT DOCUMENTS

| | | |
|---|---|---|
| 6,231,565 B1 | 5/2001 | Tovey et al. |
| 6,364,888 B1 | 4/2002 | Niemeyer et al. |
| 6,783,524 B2 | 8/2004 | Anderson et al. |
| 7,377,909 B2 | 5/2008 | Rickerd |
| 7,524,320 B2 | 4/2009 | Tierney et al. |
| 7,691,098 B2 | 4/2010 | Wallace et al. |
| 7,806,891 B2 | 10/2010 | Nowlin et al. |
| 7,824,401 B2 | 11/2010 | Manzo et al. |
| 8,221,364 B2 | 7/2012 | Voegele et al. |
| 8,479,969 B2 | 7/2013 | Shelton |
| 8,573,461 B2 | 11/2013 | Shelton et al. |
| 8,573,465 B2 | 11/2013 | Shelton |
| 8,602,288 B2 | 12/2013 | Shelton et al. |
| 8,616,431 B2 | 12/2013 | Timm et al. |
| 8,728,037 B2 | 5/2014 | Franer |
| 8,783,541 B2 | 7/2014 | Shelton et al. |
| 8,800,838 B2 | 8/2014 | Shelton |
| 8,820,605 B2 | 9/2014 | Shelton |
| 8,844,789 B2 | 9/2014 | Shelton et al. |
| 9,173,697 B2 | 11/2015 | Morrissette et al. |
| 9,301,759 B2 | 4/2016 | Spivey et al. |
| 9,572,626 B2 | 2/2017 | Verner et al. |
| 2004/0260244 A1* | 12/2004 | Piechowicz ............ A61B 17/34 604/167.06 |
| 2013/0267969 A1 | 10/2013 | Martin et al. |

\* cited by examiner

ADAPTOR FOR ROBOTICS CANNULA AND SEAL ASSEMBLY

BACKGROUND

Endoscopic procedures may be used in surgery. The term "endoscopic" refers to all types of minimally invasive surgical procedures including laparoscopic and arthroscopic procedures. Endoscopic surgery may provide reduced trauma, faster recovery, reduced risk of infection, and reduced scarring as compared to open surgery.

In order to introduce an endoscopic instrumentation into a body cavity, a device known as a "trocar" may be used to puncture and/or cannulate the wall of the body cavity. Trocars may comprise an obturator and a cannula. The obturator may include a sharply pointed or appropriately structured tip that facilitates penetration of the body cavity wall. The cannula provides a channel or opening through the body cavity wall through which endoscopic instruments may be introduced and removed by the surgeon.

Endoscopic surgery might be performed with an insufflatory fluid present within the body cavity, such as carbon dioxide, to provide adequate space to perform the intended surgical procedures. The insufflated cavity is generally under pressure and is sometimes referred to as being in a state of pneumoperitoneum. A seal or sealing arrangement can be integrally formed to a cannula, or directly attachable to the cannula, in order to maintain a state of pneumoperitoneum. The seals will generally prevent the insufflatory fluid from escaping while an endoscopic instrument may be positioned in the trocar cannula.

Some examples of trocars and related devices are disclosed in U.S. Pat. No. 5,385,553 entitled "Trocar with Floating Septum Seal," issued Jan. 31, 1995, the disclosure of which is incorporated by reference herein; U.S. Pat. No. 5,628,732 entitled "Trocar with Improved Universal Seal," issued May 13, 1997, the disclosure of which is incorporated by reference herein; U.S. Pat. No. 5,709,671 entitled "Trocar Having an Improved Tip Configuration," issued Jan. 20, 1998, the disclosure of which is incorporated by reference herein; U.S. Pat. No. 5,385,572 entitled "Trocar for Endoscopic Surgery," issued Jan. 31, 1995, the disclosure of which is incorporated by reference herein; U.S. Pat. No. 5,609,604 entitled "Trocar with Improved Blade Attachment," issued Mar. 11, 1997, the disclosure of which is incorporated by reference herein; U.S. Pat. No. 5,697,913 entitled "Trocar Including Cannula with Stepped Region," issued Dec. 16, 1997, the disclosure of which is incorporated by reference herein; U.S. Pat. No. 5,817,061 entitled "Trocar Assembly," issued Oct. 6, 1998, the disclosure of which is incorporated by reference herein; U.S. Pat. No. 5,449,370 entitled "Blunt Tipped Ultrasonic Trocar," issued Sep. 12, 1995, the disclosure of which is incorporated by reference herein; U.S. Pat. No. 8,221,364 entitled "Trocar Obturator," issued Jul. 17, 2012; and U.S. Pat. No. 8,728,037, entitled "Pleated Trocar Seal," issued on May 20, 2014, the disclosure of which is incorporated by reference herein.

Some surgical systems provide robotic control of a surgical instrument. With minimally invasive robotic surgery, surgical operations may be performed through a small incision in the patient's body. A robotic surgical system may be used with various types of surgical instruments, including but not limited to surgical staplers, ultrasonic instruments, electrosurgical instruments, and/or various other kinds of instruments, as will be described in greater detail below. An example of a robotic surgical system is the DAVINCI™ system by Intuitive Surgical, Inc., of Sunnyvale, Calif. By way of further example, one or more aspects of robotic surgical systems are disclosed in the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; and U.S. Pat. No. 7,824,401, entitled "Surgical Tool With Writed Monopolar Electrosurgical End Effectors," issued Nov. 2, 2010, the disclosure of which is incorporated by reference herein.

Additional examples of instruments that may be incorporated with a robotic surgical system are described in U.S. Pub. No. 2013/0012957, entitled "Automated End Effector Component Reloading System for Use with a Robotic System, published Jan. 10, 2013, now U.S. Pat. No. 8,844,789, issued Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued Sep. 2, 2014, the disclosure of which is incorporated by reference herein; U.S. Pub. No. 2012/0132450, entitled "Shiftable Drive Interface for Robotically-Controlled Surgical Tool," published May 31, 2012, now U.S. Pat. No. 8,616,431, issued Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, now U.S. Pat. No. 8,573,461, issued Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, now U.S. Pat. No. 8,602,288, issued Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued Apr. 5, 2016, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, U.S. Pat. No. 8,479,969, issued Jul. 9, 2013; U.S. Pub. No. 2012/0138660, entitled "Robotically-Controlled Cable-Based Surgical End Effectors," published Jun. 7, 2012, now U.S. Pat. No. 8,800,838, issued Aug. 12, 2014, the disclosure of which is incorporated by reference herein; U.S. Pub. No. 2012/0205421, entitled "Robotically-Controlled Surgical End Effector System with Rotary Actuated Closure Systems," published Aug. 16, 2012, now U.S. Pat. No. 8,573,465, issued as Nov. 5, 2013, the disclosure of which is incorporated by reference herein; U.S. patent application Ser. No. 13/443,101, entitled "Control Interface for Laparoscopic Suturing Instrument," filed Apr. 10, 2012, now U.S. Pat. No. 9,814,457, issued Nov. 14, 2017, the disclosure of which is incorporated by reference herein; and U.S. Provisional Pat. App. No. 61/597,603, entitled "Robotically Controlled Surgical Instrument," filed Feb. 10, 2012, the disclosure of which is incorporated by reference herein.

It may be desirable to provide an adapter for coupling modular trocar seal assembly with a trocar cannula that is made for use in a robotic surgical system.

BRIEF DESCRIPTION OF THE DRAWINGS

The accompanying drawings, which are incorporated in and constitute a part of the specification, illustrate embodiments of the invention, and, together with the general description of the invention given above, and the detailed description of the embodiments given below, serve to explain the principles of the present invention.

Figure 1:
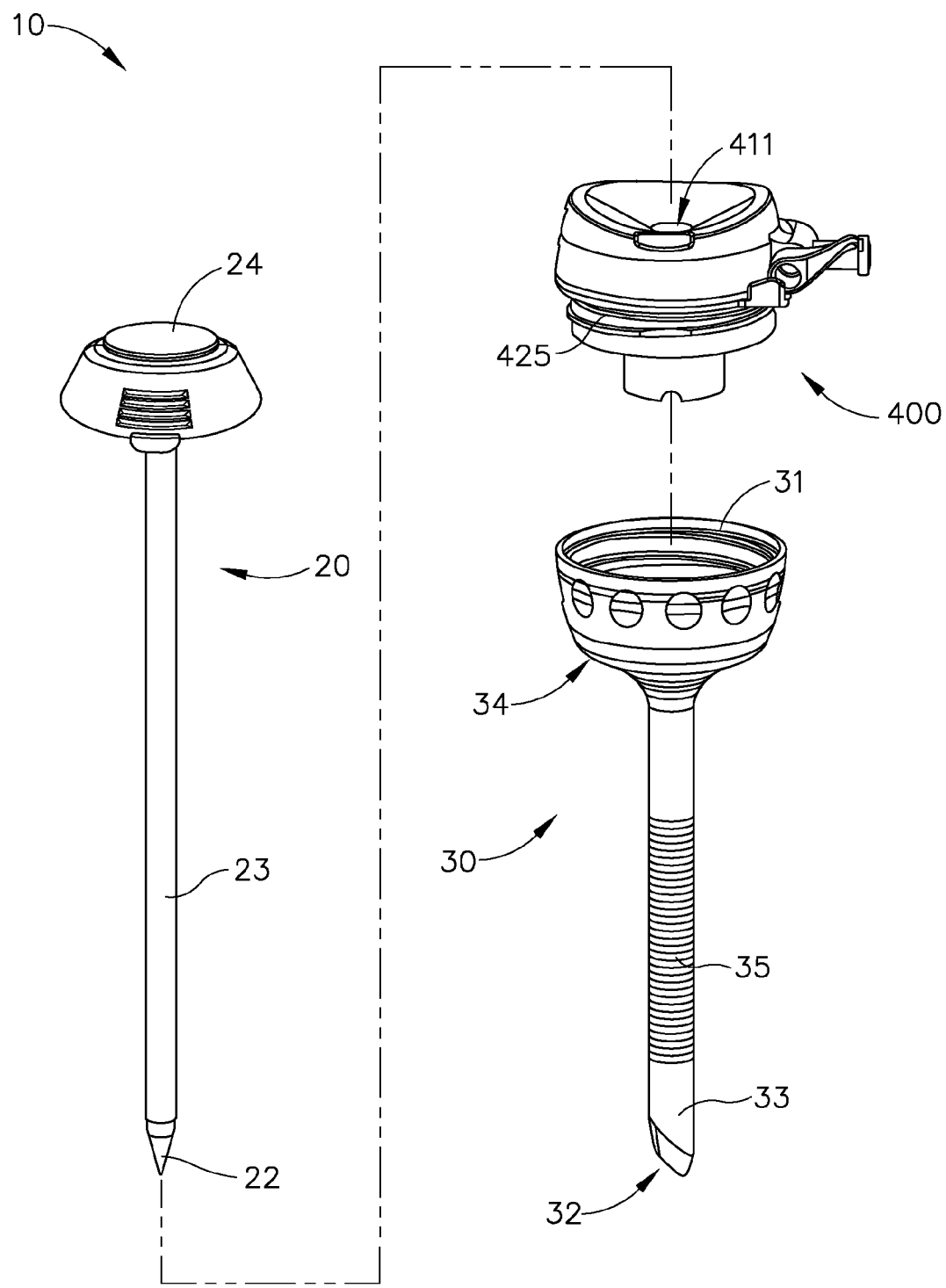
FIG. 1 depicts an exploded view of an exemplary trocar.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

1. Exemplary Trocar

Figure 2:
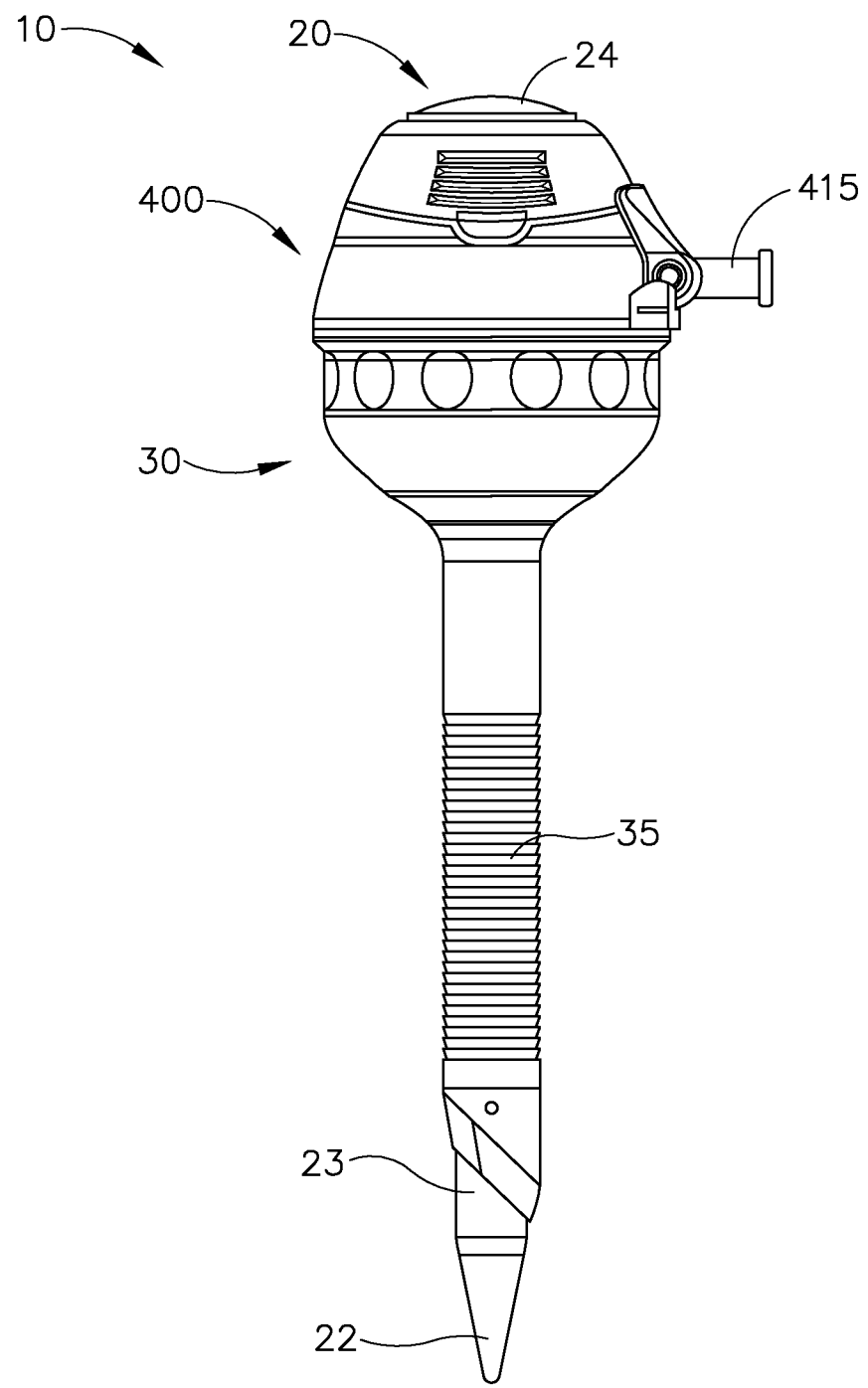
FIG. 2 depicts a side elevational view of the trocar of FIG. 1, with the obturator positioned through the seal assembly and cannula and attaching to the top of the seal assembly.

FIGS. 1-2 show an exemplary trocar instrument (10) that is sized for providing an access port for performance of minimally invasive surgery. Trocar instrument (10) includes an obturator (20), a cannula (30), and a seal assembly (400). Obturator (20) includes an obturator grip (24) for grasping by the operator, a shaft portion (23), and an obturator tip (22). As shown in FIG. 2, obturator (20) is configured for insertion through seal assembly (400) and cannula (30) such that obturator tip (22) passes through seal assembly (400) and cannula (30), with obturator tip (22) extending distally past the distal end of cannula (35) to thereby enable obturator tip (22) to penetrate or dissect through tissue layers of a patient to provide an opening adjacent to the surgical site. Shaft portion (23) is rigid to withstand force exerted by tissue layers during penetration and dissection through the tissue. Obturator tip (22) is configured to provide sufficient pressure to facilitate the penetration or dissection of tissue layers as obturator (20) is inserted through the tissue layers toward the surgical site, and is therefore shaped to enlarge an opening in the tissue as trocar instrument (10) is inserted toward the internal surgical site.

After obturator (20) and cannula (30) are inserted through the tissue, obturator (20) is removed from the rest of trocar instrument (10), while cannula (30) remains within the tissue to provide a pathway for insertion of instruments within the body cavity of the patient to perform minimally invasive surgery. Cannula (30) includes threading (31) for coupling with seal assembly (400), a seal assembly housing (34), a hollow shaft (33) distal to seal assembly housing (34), ridges (35) along the outer surface of hollow shaft (33), and an open tip (32) configured to enable surgical instruments to access the surgical site. When obturator (20) is removed from the surgical site, hollow shaft (33) maintains the opening adjacent to the surgical site. Ridges (35) are configured to provide extra stability for trocar instrument (10) by providing additional contact to the surrounding tissue layers of the patient. Ridges (35) may be particularly helpful in providing stability when pressurized insufflation fluid (e.g., pressurized air, etc.) is introduced to the surgical site, since the insufflation may provide a natural tendency to push cannula (30) away from the surgical site.

Seal assembly (400) allows for obturator (20) or surgical instruments to access the surgical site via cannula (30) while simultaneously maintaining pneumostasis of the body cavity of the patient by preventing or minimizing escape of pressurized insufflation fluid from the body cavity of the patient. In trocar instrument (10) of the present example, seal assembly (400) includes threading (425) for coupling with cannula (30), an instrument port (411), and a valve (414). Valve (414) is configured to permit the operator to selectively introduce or relieve pressurized insufflation fluid through trocar instrument (10) into the body cavity of the patient.

Figure 3:
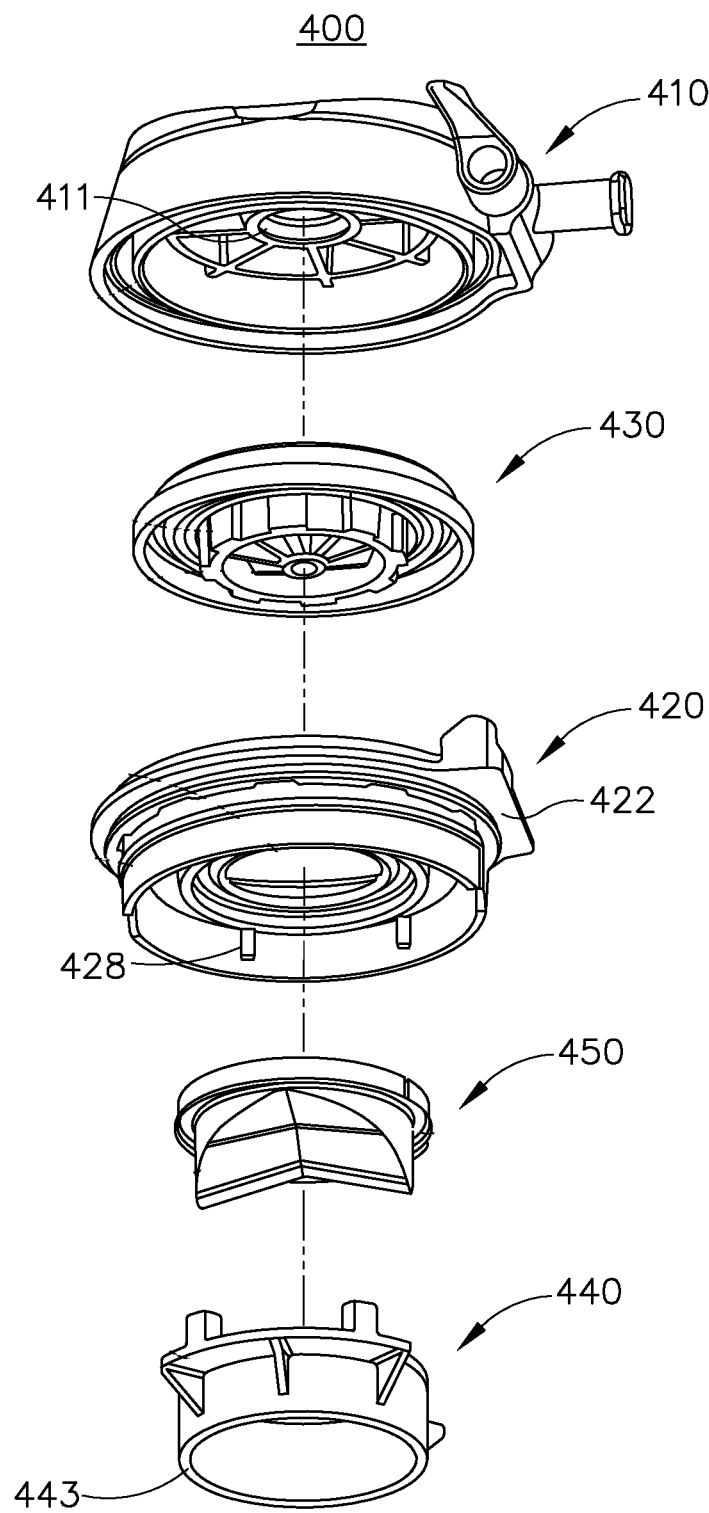
FIG. 3 depicts an exploded view of the seal assembly of the trocar of FIG. 1, as viewed from below the seal assembly.
Figure 4:
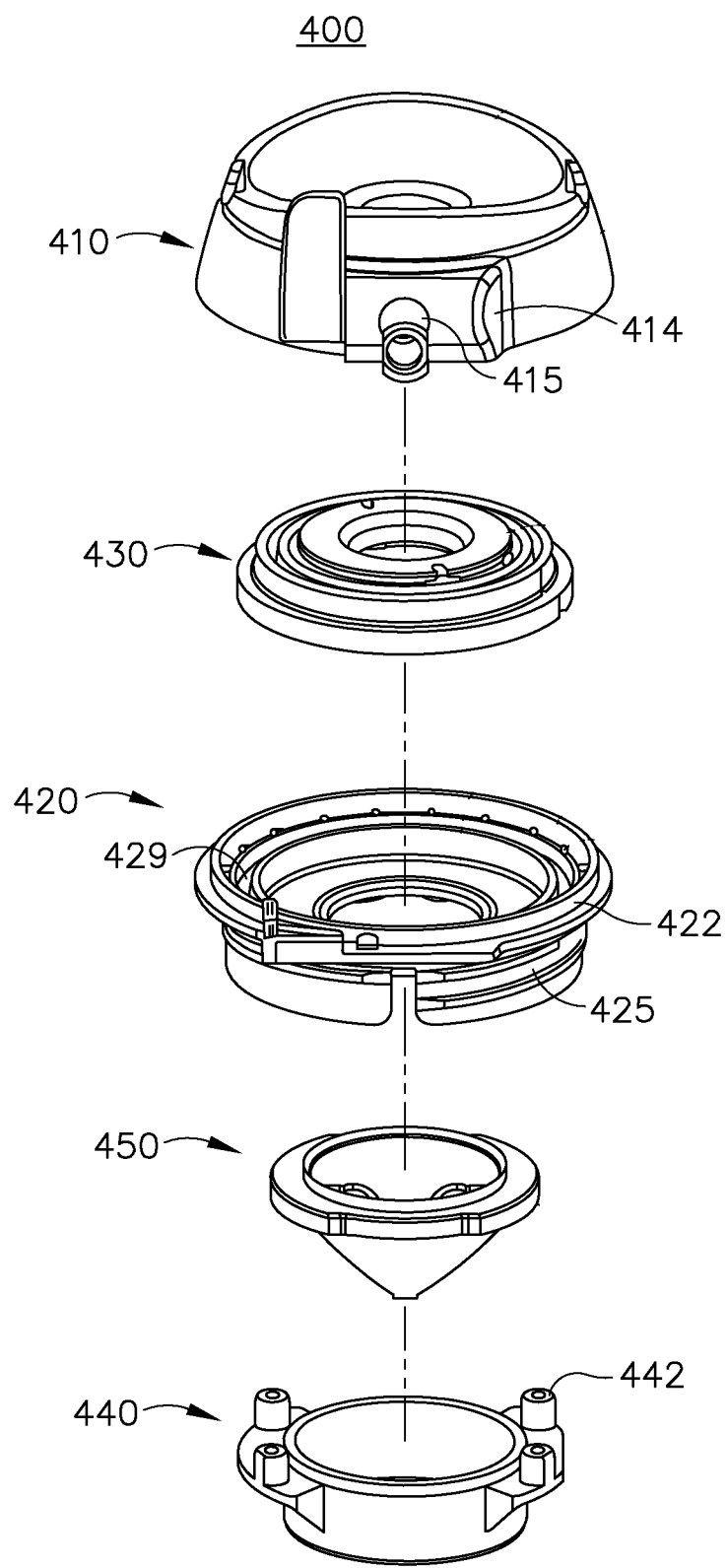
FIG. 4 depicts another exploded view of the seal assembly of FIG. 3, as viewed from above the seal assembly.
Figure 5:
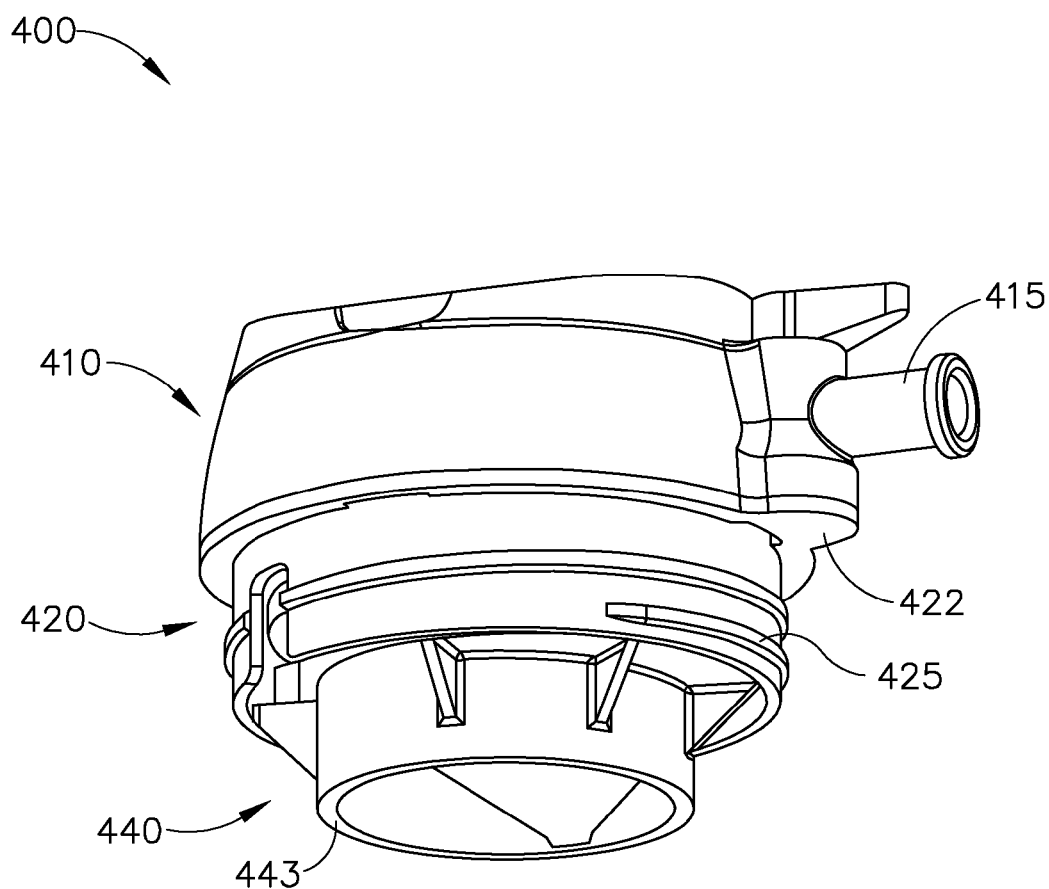
FIG. 5 depicts a perspective view of the seal assembly of FIG. 3.

FIGS. 3-4 show seal assembly (400) in greater detail. As shown, seal assembly (400) further includes a top valve housing (410), a connecting ring (420), an instrument seal (430), a closure valve base (440), and a closure valve (450). Top valve housing (410) includes instrument port (411), an insufflation fluid port (415), and valve (414). Instrument port (411) provides access for obturator (20) or a surgical instrument to the surgical site. Insufflation fluid port (415) is in fluid communication with top valve assembly (414) so that the insufflation fluid may pass through top valve assembly (414), around instrument seal (430) and the proximal face of closure valve (450), through cannula (30), out open tip (32) and to the surgical site in order to provide an insufflated body cavity in the patient.

Instrument seal (430) and closure valve (450) form a sealing arrangement that work together to maintain pneumostasis in the insufflated body cavity of the patient. In this example, closure valve (450) is a "duck bill" valve. However, other types of closure valves may also be used, including flapper valves, etc. When an endoscopic instrument is passed through closure valve (450), closure valve (450) will open but will generally not provide a complete seal against the instrument. When the endoscopic instrument is removed from trocar instrument (10), closure valve (450) closes and substantially prevents insufflation fluid from escaping trocar instrument (10). To supplement closure valve (450) when obturator (20) or an endoscopic surgical instrument is inserted through seal assembly (400), instrument seal (430) seals against the inserted obturator (20) or endoscopic surgical instrument to prevent insufflation fluid from escaping through trocar instrument (10). However, instrument seal (430) generally will not maintain pneumostasis on its own unless obturator (20) or endoscopic instrument is positioned in trocar instrument (10). Therefore, instrument seal (430) and closure valve (450) may together maintain a state of pneumostasis regardless of whether obturator (20) or an endoscopic surgical instrument is disposed in trocar instrument (10).

Connecting ring (420) simultaneously connects seal assembly (400) with cannula (30) while also providing sealing surfaces for instrument seal (430) and closure valve (450). Connecting ring (420) has outer threading (425) that is compatible with threading (31) of cannula (30). Connecting ring (420) also has a plurality of inserts (428) on its distal side that are compatible with a plurality of pillars (442) present on closure valve base (440). This allows for connecting ring (420) and closure valve base (440) to effectively provide a seal around the perimeter of closure valve (450). Similarly, top valve housing (410) and connecting ring (420) also come together with instrument seal (430) in between to provide a seal around the perimeter of instrument seal (430).

Figure 6:
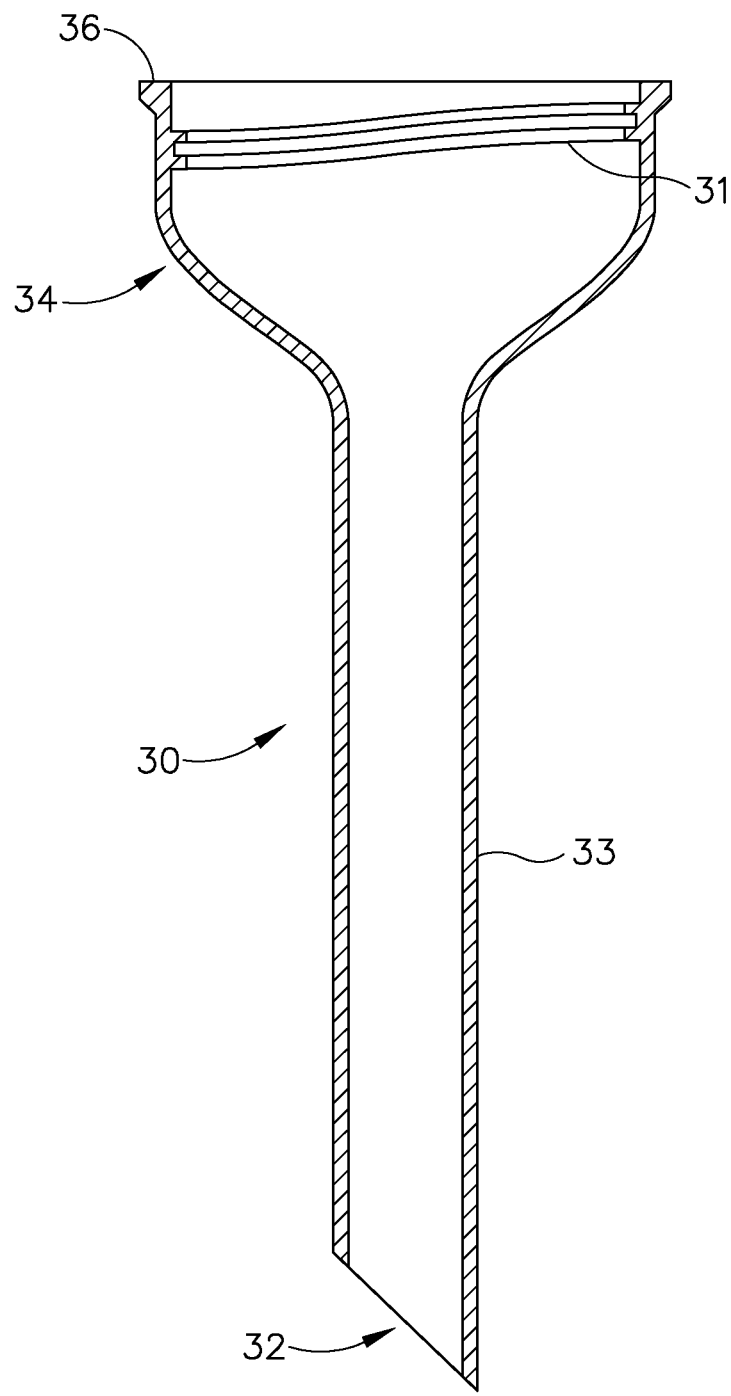
FIG. 6 depicts a cross-sectional side view of an exemplary reusable cannula of the trocar of FIG. 1, with threads at the proximal end configured for attachment with the seal assembly of FIG. 3.
Figure 7:
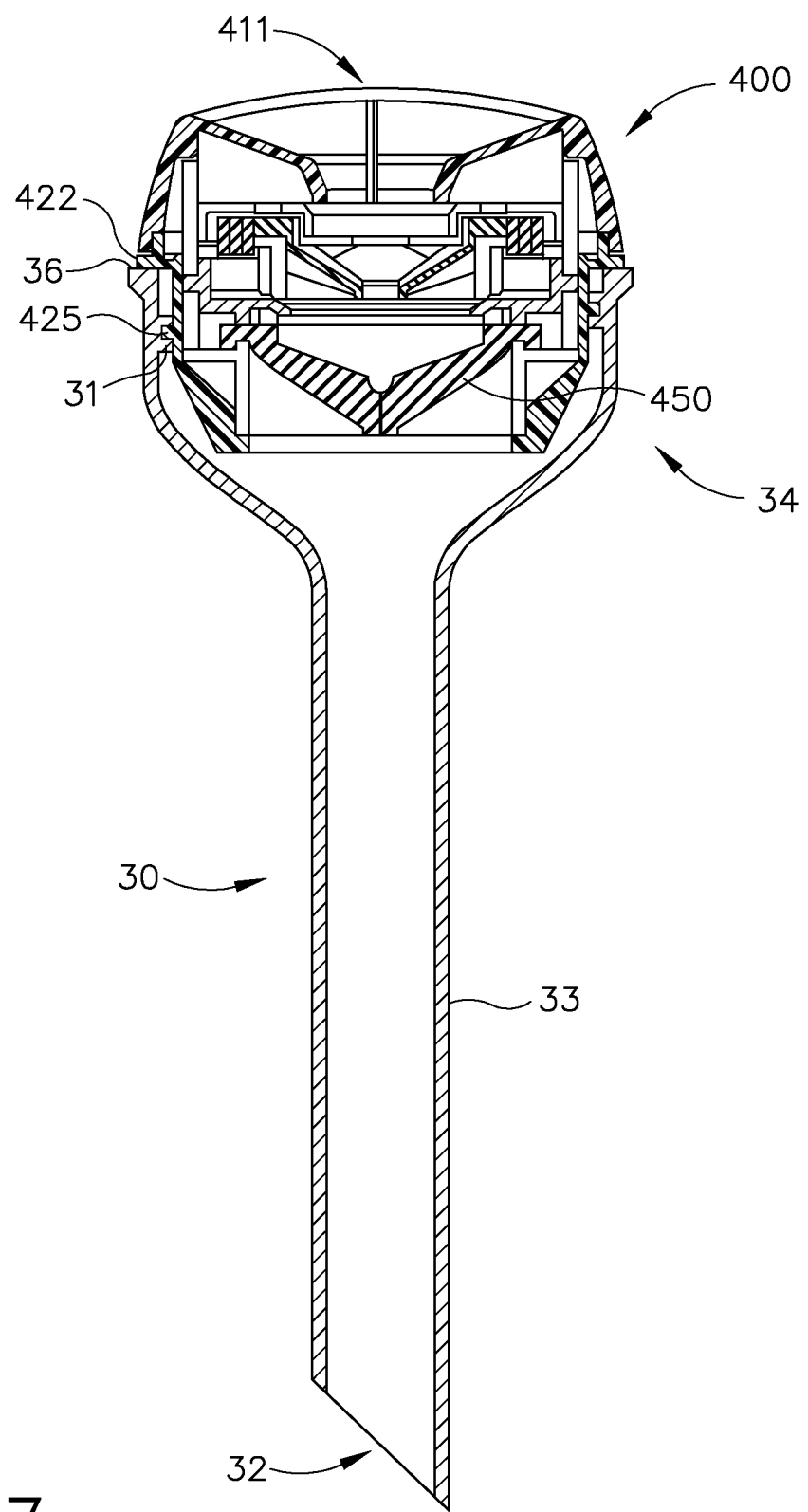
FIG. 7 depicts a cross-sectional side view of the cannula of FIG. 6 coupled with the seal assembly of FIG. 3, and without an obturator present.

In order to maintain pneumostasis in the insufflated body cavity of the patient, the contact point between proximal lip of the cannula (36), as shown in FIG. 6, and some distal surface (422, 443) of seal assembly (400) may effectively create a seal. FIG. 7 shows cannula (30) coupled with seal assembly (400) via compatible threading (425, 31). Compatible threading (425, 31) extends far enough along the interior of cannula (30) to provide sufficient force to create a seal between distal surface (422) of seal assembly (400) and proximal lip of the cannula (36). In order to further facilitate this seal, an elastomeric material may be used, such as an o-ring (not shown), in between proximal lip of cannula (36) and distal surface (510) of seal assembly (500).

In addition to or in lieu of the foregoing, the various components and features of trocar assembly (10) may be constructed and operable in accordance with at least some of the teachings of U.S. Pat. No. 5,385,553; U.S. Pat. No. 5,628,732; U.S. Pat. No. 5,709,671; U.S. Pat. No. 5,385,572; U.S. Pat. No. 5,609,604; U.S. Pat. No. 5,697,913; U.S. Pat. No. 5,817,061; U.S. Pat. No. 5,449,370; U.S. Pat. No. 8,221,364; and/or U.S. Pat. No. 8,728,037. The disclosure of each of those patents is incorporated by reference herein.

II. Exemplary Robotic Cannula

Figure 8:
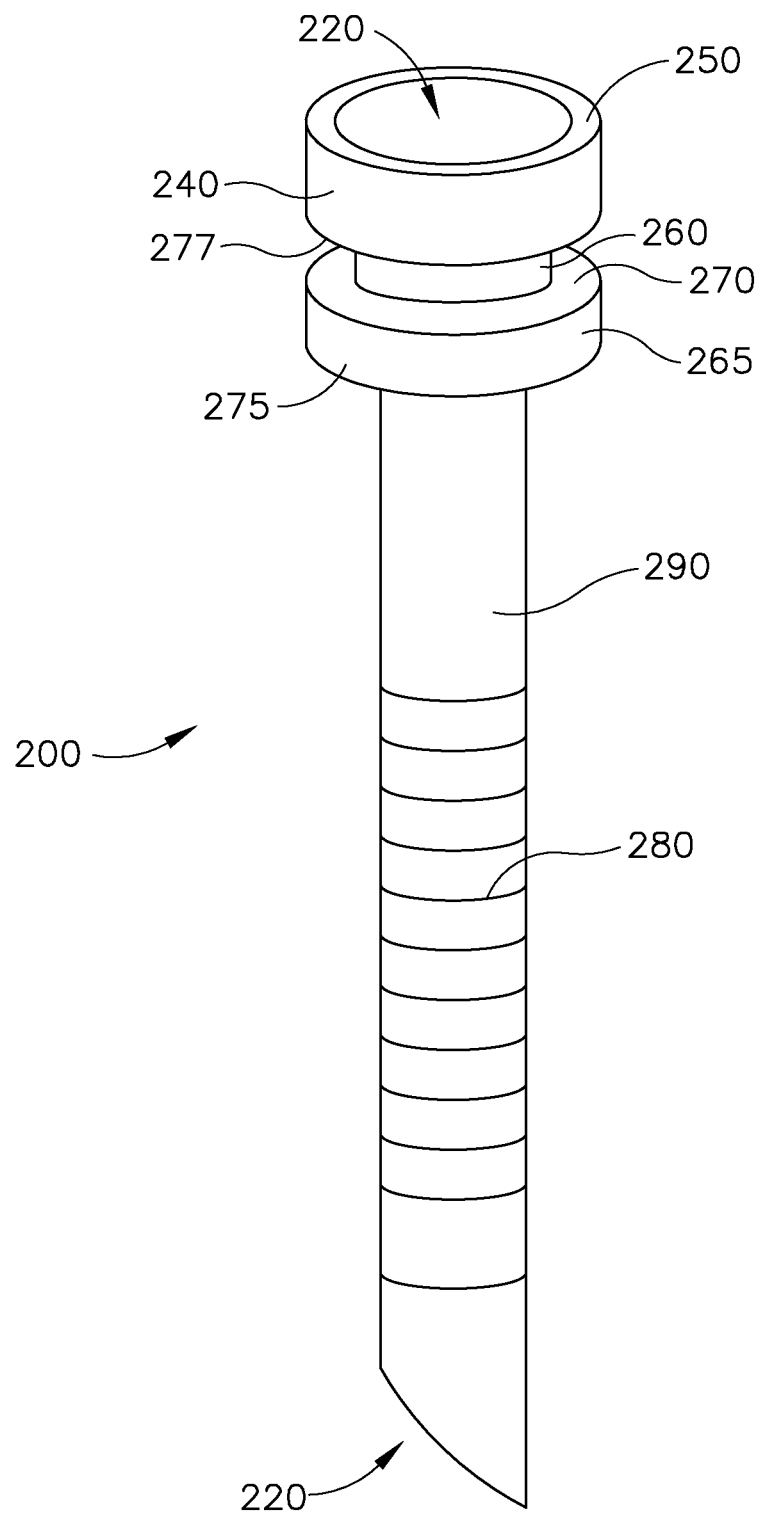
FIG. 8 depicts a perspective view of an exemplary reusable cannula configured for use in a robotic surgical system.
Figure 9:
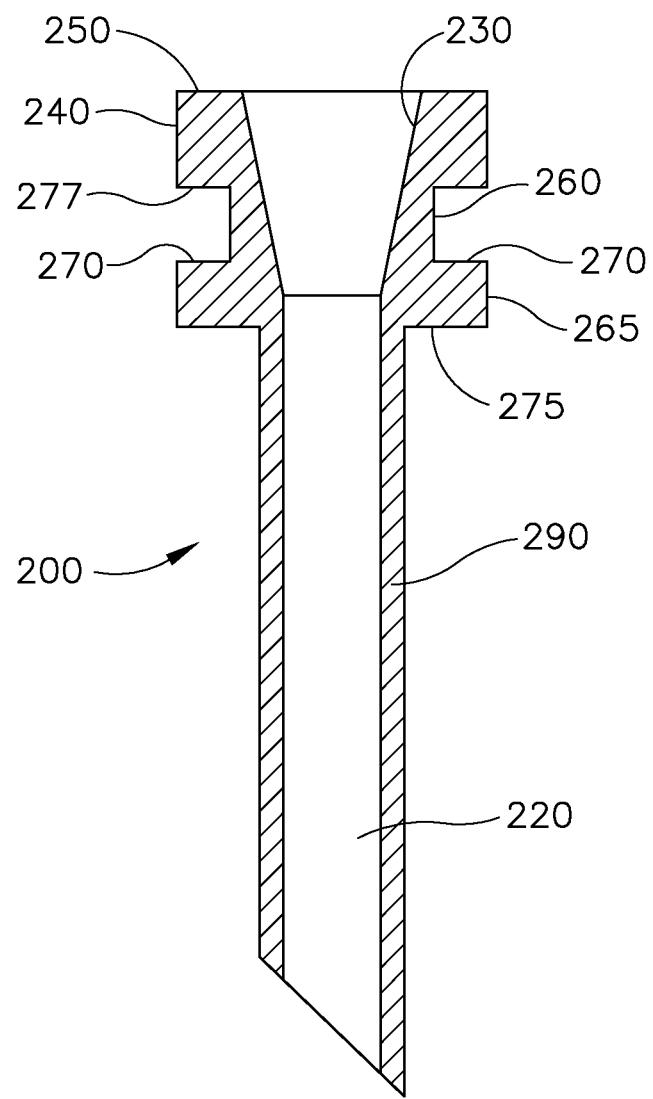
FIG. 9 depicts a cross-sectional side view of the cannula of FIG. 8.

FIGS. 8-9 show another exemplary cannula (200). Cannula (200) of this example is configured for use with a robotic surgical system such as the robotic surgical systems described in U.S. Pat. No. 6,364,888; U.S. Pat. No. 7,524,320; and U.S. Pat. No. 7,806,891. The disclosure of each of those patents is incorporated by reference herein. By way of example only, cannula (200) may be constructed and operable in accordance with at least some of the teachings of U.S. Pub. No. 2012/0078245, entitled "Cannula," published Mar. 29, 2012, now U.S. Pat. No. 9,173,697, issued Nov. 3, 2015, the disclosure of which is incorporated by reference herein. Similar to cannula (30) described above, cannula (200) of this example has a proximal angled opening (230) leading to a hollow shaft (290), ridges (280), and an open tip (220) that is configured to enable surgical instruments to access the surgical site. Hollow shaft (290) defines a longitudinal axis. However, cannula (200) differs from cannula (30) described above as it does not have seal assembly housing (34) configured for supporting seal assembly (400). Instead of having seal assembly housing (34) at the proximal end of cannula (200), there are two raised, annular flanges (240, 265) and a mounting section (260) that are configured to mate with cannula mounting bracket jaws (not shown). The annular flanges (240, 265) define lips (250, 277, 270, 275) that are substantially perpendicular to the longitudinal axis defined by hollow shaft (290). Cannula mounting bracket jaws (not shown) reach part way around annular flanges (240, 265) and mounting section (260) in order to secure cannula (200) to a manipulator arm (not shown) of the robotic surgical system.

Figure 10:
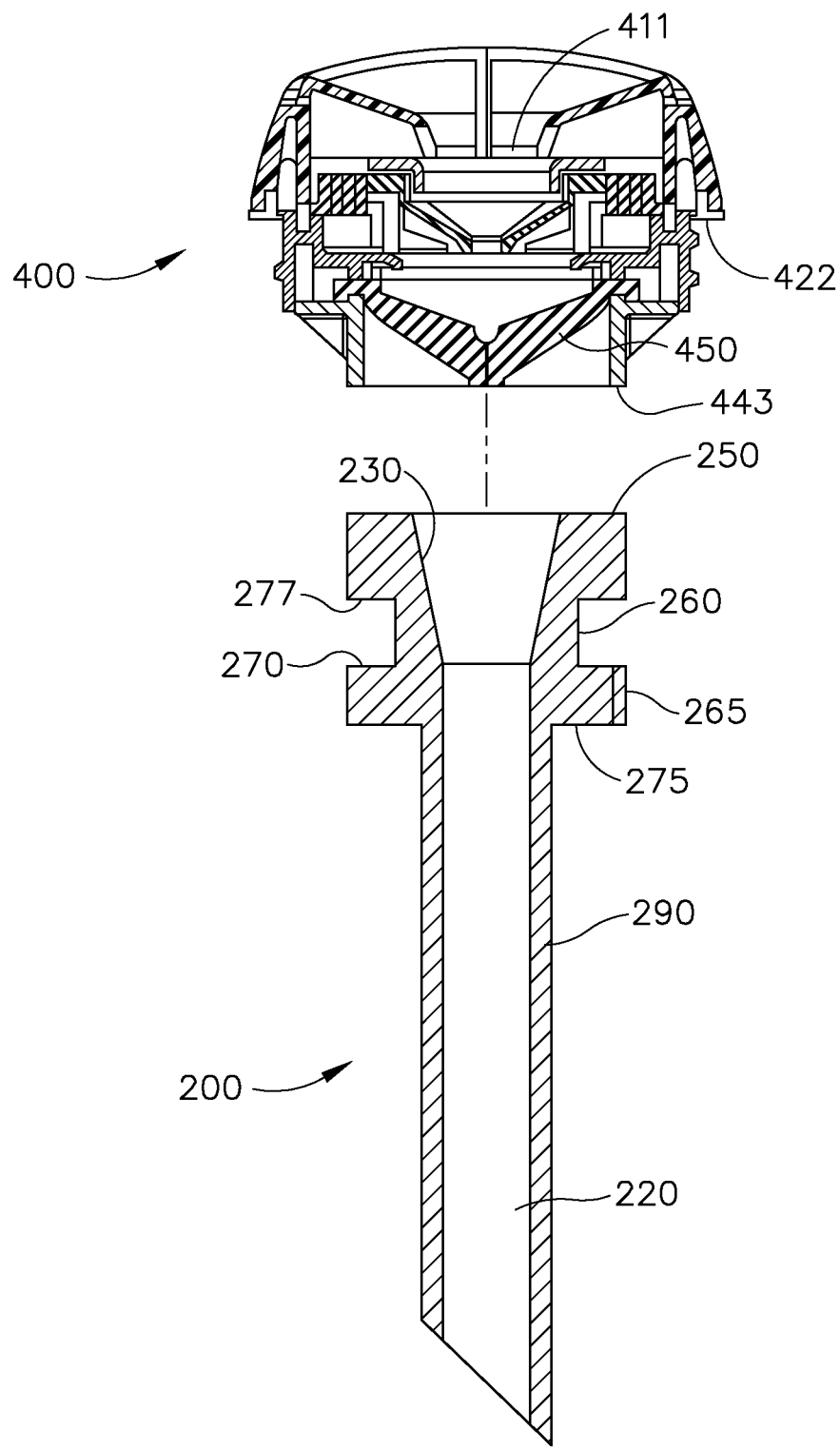
FIG. 10 depicts a cross-sectional side view of the seal assembly of FIG. 3 positioned over the cannula of FIG. 8.

Since cannula (200) includes annular flanges (240, 265) and a mounting section (260) instead of seal assembly housing (34) in order to provide robotic manipulation, seal assembly (400) might not be directly compatible with cannula (200). As shown in FIG. 7, cannula (30) of the previous example has seal assembly housing (34) to support seal assembly (500); and compatible threading (31) and proximal lip (36) configured to mate with distal surface (510) of seal assembly (500). All of these features help provide a sealed connection between the seal assembly and the cannula in order to maintain pneumostasis. By contrast, FIG. 10 shows an exemplary seal assembly (400) positioned over cannula (200) of the present example. While cannula (200) has lip (250) capable of contact with at least one distal surface (443)

of seal assembly (400), cannula (200) is lacking a compatible housing for providing support for seal assembly (400) and a means to provide enough force to create a sufficient sealed connection to maintain pneumostasis. Thus, some additional component is required in order to provide an appropriate coupling between seal assembly (500) and cannula (200). An example of such a component is described in greater detail below.

III. Exemplary Adaptor for Seal Assembly and Robotic Cannula

Figure 11:
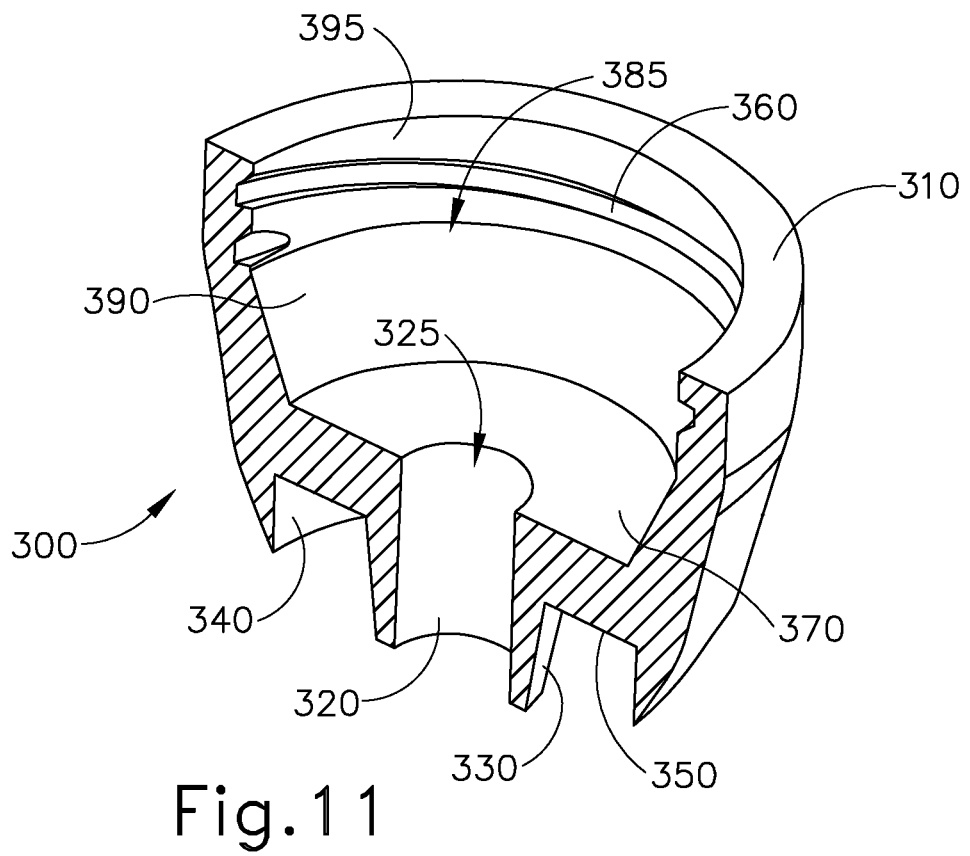
FIG. 11 depicts a cross-sectional perspective view of an exemplary seal assembly adaptor configured for coupling the seal assembly of FIG. 3 with the cannula of FIG. 8.
Figure 12:
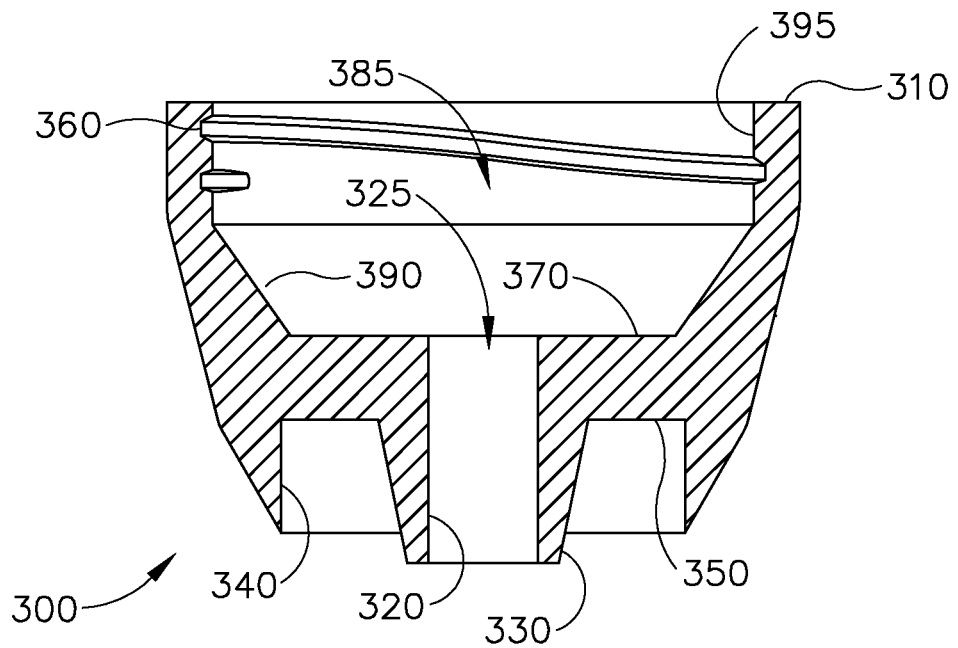
FIG. 12 depicts a cross-sectional side view of the adaptor of FIG. 11.

FIGS. 11-12 show an adaptor (300) for connecting cannula (200) with a seal assembly (400) while maintaining pneumostasis in an insufflated body cavity of a patient. Adaptor (300) includes a seal assembly housing (385) defined by a housing floor (370), a housing ramp (390), and a housing wall (395). Adaptor (300) is composed of a rigid plastic, such as Radel, and has threading (360) that is compatible with threading (425) of seal assembly (400). Of course, many kinds of rigid plastic material maybe used and will be apparent to a person having ordinary skill in the art. Some examples of possible rigid plastic material include but are not limited to SustaPEEK MG, Susta PEI MG, and Polysulfone. This compatible threading (360, 425) allows for proximal end (310) of adaptor (300) and distal surface (422) of seal assembly (400) to couple together, effectively creating a seal to maintain pneumostasis. However, adaptor (300) could be made entirely of an elastomeric material with dimensions configured to create interference between threading (530) of seal assembly (500) and housing wall (395) of adaptor (300), creating a seal to maintain pneumostasis. Therefore, threading (360) might not necessarily be required on adaptor (300). Elastomeric material may be used in addition to or in lieu of using rigid plastic. In some versions of adaptor (300), an elastomeric component, such as an o-ring (not shown), is positioned between proximal end (310) of adaptor (300) and distal surface (422) of the seal assembly (400) to provide or enhance a seal between proximal end (310) and distal surface (422), further maintaining pneumostasis.

Adaptor (300) further includes a channel (325) defined by a channel surface (320). Channel (325) allows for obturator (20) or a surgical instrument to pass from seal assembly (400) to cannula (200) via adaptor (300) to thereby access a surgical site. Channel (325) further provides a pathway for fluid communication between seal assembly (500) and cannula (200).

Adaptor (300) also has two annular walls, an exterior taper (340), and an interior taper (330), both tapers (330, 340) being located below housing floor (370). Exterior taper (340) may have an inner diameter that is less than the outer diameter of flange (240). In some versions, the distal end of interior taper (330) may have an outer diameter that is less than the inner diameter of proximal angled opening (230); while the proximal end of interior taper (330) may have an outer diameter that is greater than the inner diameter of proximal angled opening (230). In other words, interior taper (330) may taper at an angle that is wider than the taper angle of proximal angled opening (230). This may provide for an enhanced interference fit. Together, exterior taper (340) and interior taper (330) terminate at a trocar roof (350). Interior taper (330) is sized with a circumference to fit inside proximal angled opening (230) of the cannula (200), and is tapered at an angle similar to that of interior wall defining proximal angled opening (230). Exterior taper (340) is sized with a circumference to complement the circumference of flange (240), and a depth not exceeding the depth of flange (240). Due to the circumferences of exterior taper (340) and interior taper (330), trocar roof (350) complements lip (250) of cannula (200).

Figure 13A:
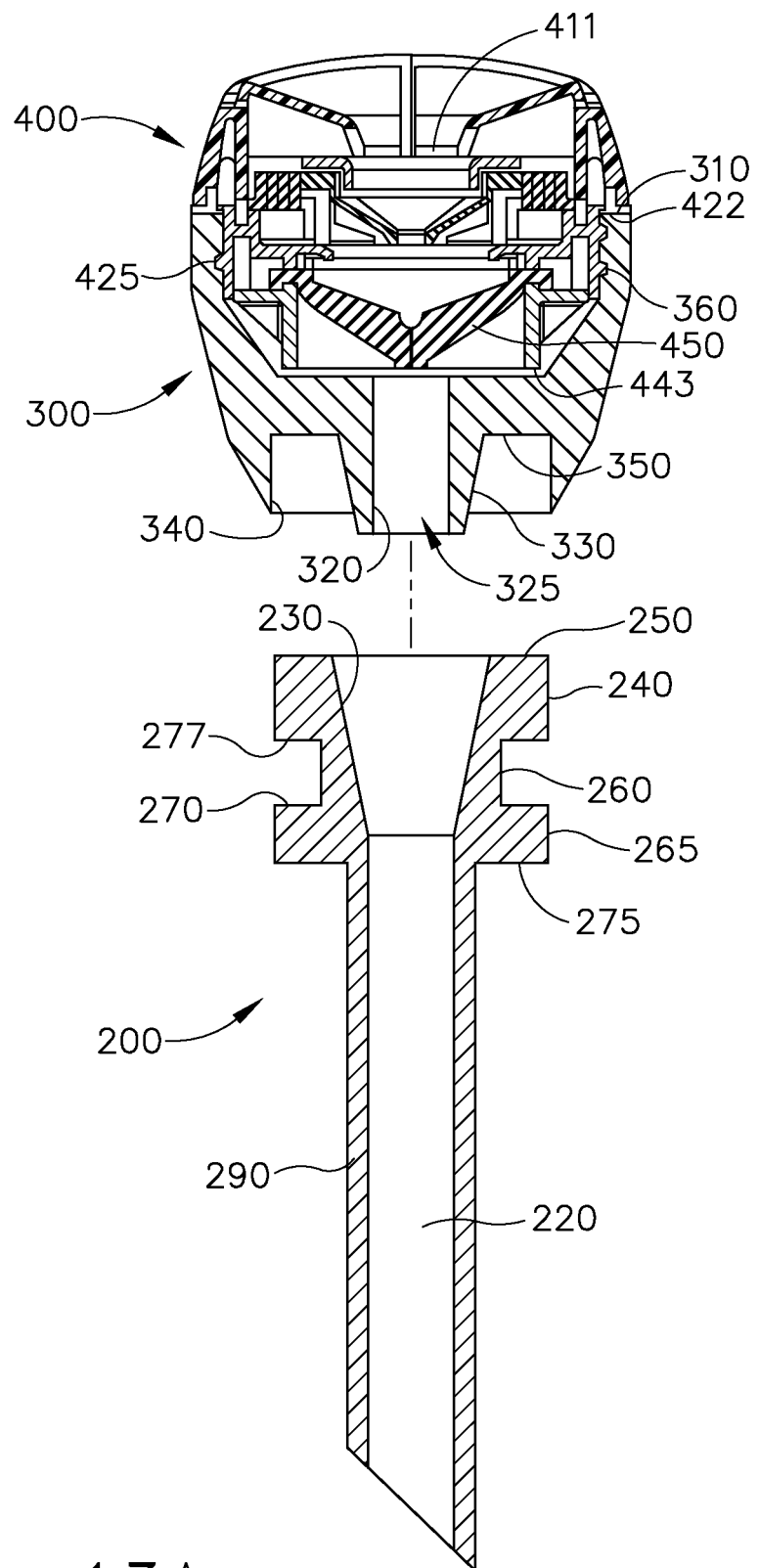
FIG. 13A depicts an exploded cross-sectional side view of the adaptor of FIG. 11 attached to the seal assembly of FIG. 3, positioned above the cannula of FIG. 8.

FIG. 13A shows adaptor (300) connected to seal assembly (400). Threading (360) of adaptor (300) is connected to threading (425) of seal assembly (400). Through this engagement of threading (425, 360), connections between distal surface (422) of seal assembly (400) and proximal end (310) of adaptor (300) are sufficient to provide a seal maintaining pneumostasis in an insufflated body cavity of a patient. Also, seal assembly housing (385) is supporting seal assembly (400), so that if adaptor (300) is stable, so is seal assembly (400).

Figure 13B:
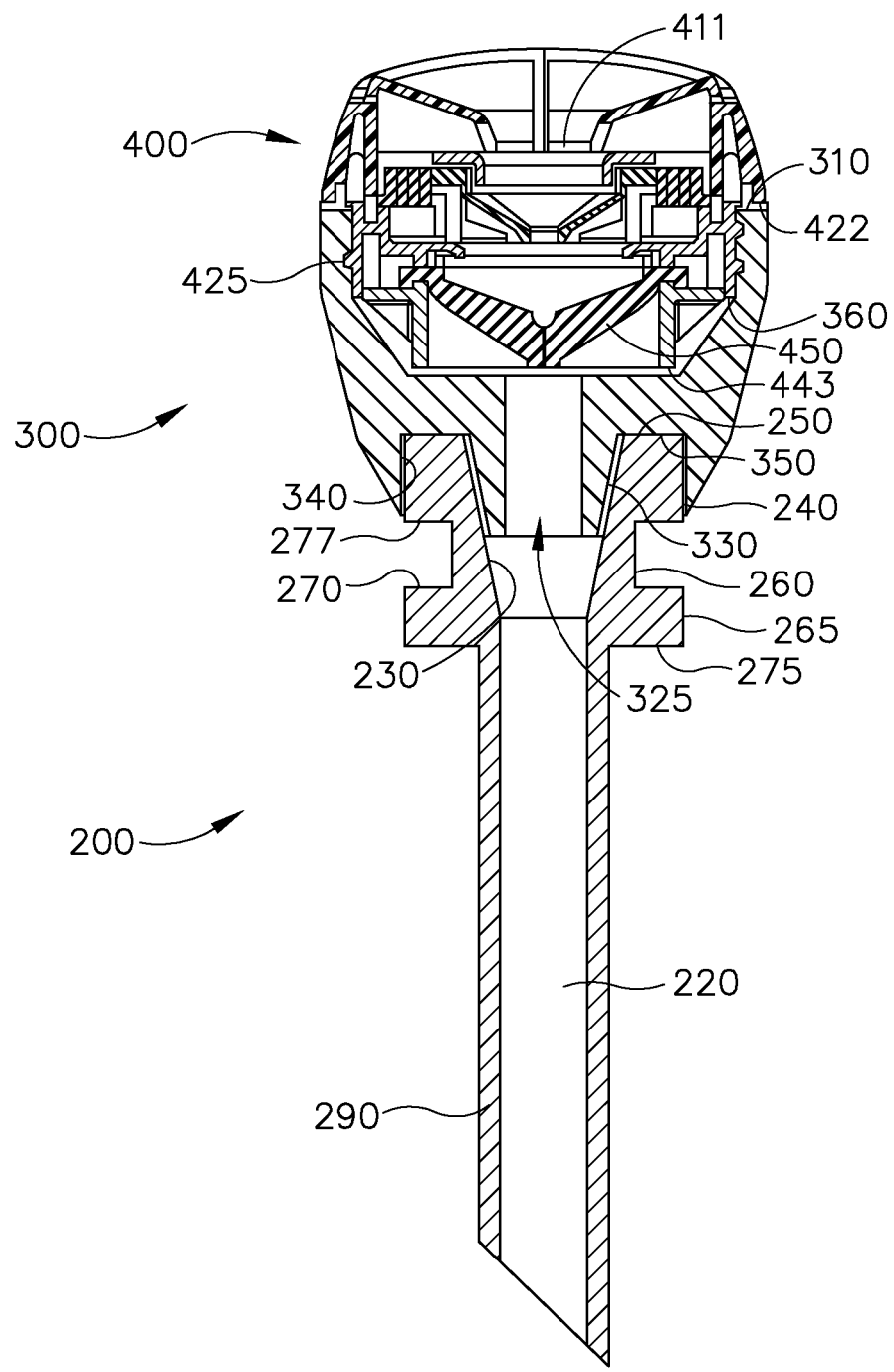
FIG. 13B depicts a cross-sectional side view of the adaptor of FIG. 11 attached to the seal assembly of FIG. 3, further coupled with the cannula of FIG. 8.

FIG. 13B shows the complementary geometry of adaptor (300) interacting with cannula (200). A seal between adaptor (300) and flange (240) maintaining pneumostasis can be created using multiple materials. If adaptor (300) is made entirely out of elastomeric material, interior taper (330) could be dimensioned for interference with interior wall defining proximal angled opening (230), exterior taper (340) could be dimensioned for interference with flange (240), or both interior taper (330) and exterior taper (340) could be dimensioned for interference with interior wall defining proximal angled opening (230) and flange (240) respectively. All of these possibilities could create a seal, in effect maintaining pneumostasis in an insufflated body cavity of a patient.

Adaptor (300) could be partially made from a rigid body. If so, there could be elastomeric material overmolded around interior taper (330) where the overmold is dimensioned for interference with interior wall defining proximal angled opening (230). There could also be elastomeric material overmolded around exterior taper (340) where overmold is dimensioned for interference with flange (240). There could be elastomeric material overmolded around both interior taper (330) and exterior taper (340), where overmold is dimensioned for inference with interior wall defining proximal angled opening (230) and flange (240) respectively. Again, all of these possibilities could create a seal, in effect maintaining pneumostasis in an insufflated body cavity of a patient.

Figure 13C:
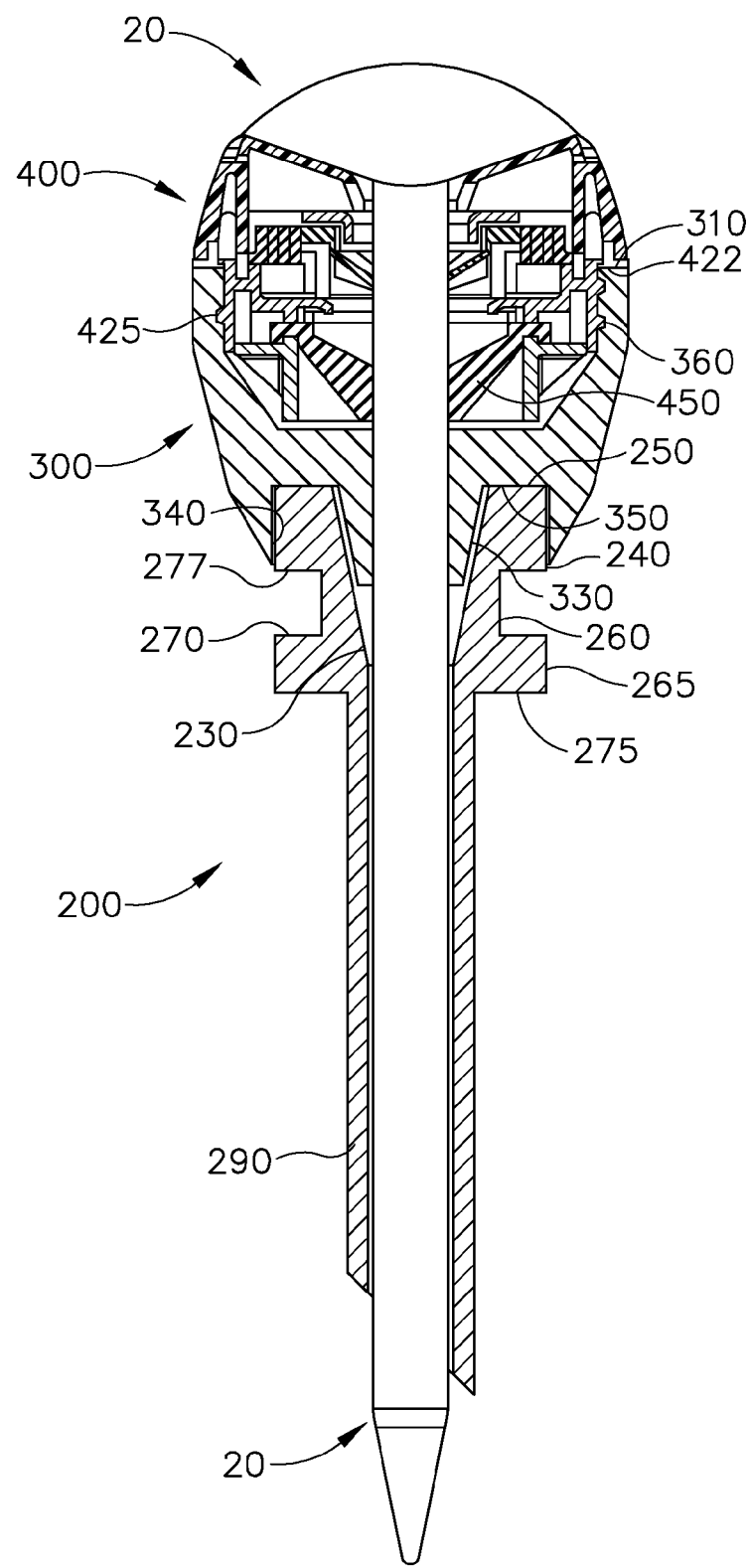
FIG. 13C depicts a cross-sectional side view of the adaptor of FIG. 11 attached to the seal assembly of FIG. 3, further coupled with the cannula of FIG. 8, with an obturator positioned through the seal assembly, adaptor, and cannula.

Adaptor (300) could be made entirely from a rigid body, and an elastomeric o-ring could be added in between any of the contact points of cannula (200) and adaptor (300). For instance, an elastomeric o-ring could be added in between interior taper (330) and interior wall defining proximal angled opening (230). Or, there could be an elastomeric o-ring in between exterior taper (340) and flange (240). Additionally, there could be an elastomeric o-ring in between trocar roof (350) and lip (250) of cannula (200). All of these possibilities or combinations thereof are capable of creating a seal between the adaptor (300) and the cannula (200). If cannula (200) has threading (not shown), adaptor (300) could be modified to have complementary threading (not shown) in order to create the necessary force to maintain pneumostasis. However, a person having ordinary skill in the art would recognize other methods of creating necessary force to maintain pneumostasis, such as but not limited to latches and snap-fitting features. FIG. 13C shows how adaptor (300) provides a path for insertion of obturator (20) through seal assembly (400), adaptor (300), and cannula (200), with the ability to maintain pneumostasis in an insufflated body cavity of a patient.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a seal assembly housing, wherein seal assembly housing comprises a proximal end and a distal end;
   (b) a channel, wherein the channel defines a longitudinal axis, wherein the channel comprises a proximal end and a distal end, wherein the proximal end of the channel is in fluid communication with the distal end of the seal assembly housing;
   (c) an interior tapered surface encompassing at least the distal end of the channel, wherein the interior tapered surface comprises a proximal end and a distal end, wherein the proximal end has a larger perimeter than the distal end;
   (d) an exterior tapered surface, wherein the exterior tapered surface comprises a proximal end and a distal end;
   (e) a trocar roof, wherein the trocar roof is defined between the termination of proximal ends of the interior tapered surface and the exterior tapered surface; and
   (f) a hollow cannula, wherein the cannula comprises an annular flange, wherein the outer perimeter of the annular flange comprises threading, wherein the exterior tapered surface further comprises threading configured to complement threading on the outer perimeter of the annular flange of the cannula.

2. The apparatus of claim 1, wherein the apparatus is formed entirely of elastomeric material.

3. The apparatus of claim 2, wherein the apparatus further comprises a hollow cannula, wherein the cannula comprises an annular flange with a proximal angled opening, wherein the interior tapered surface is configured to provide an interference fit with the proximal angled opening of the cannula.

4. The apparatus of claim 3, wherein the exterior tapered surface is configured for interference with an outer perimeter of the annular flange of the cannula.

5. The apparatus of claim 2, wherein the apparatus further comprises a hollow cannula, wherein the cannula comprises an annular flange, wherein the exterior tapered surface is configured to provide an interference fit with an outer perimeter of the annular flange of the cannula.

6. The apparatus of claim 1, wherein the apparatus is formed partially of a rigid material and partially of an elastomeric material.

7. The apparatus of claim 1, wherein the seal assembly comprises threading, wherein the seal assembly housing further comprises threading configured to complement the threading of the seal assembly.

8. The apparatus of claim 1, wherein the apparatus further comprises a hollow cannula, wherein the cannula comprises an annular flange with a proximal angled opening, wherein the interior tapered surface comprises elastomeric material, wherein the elastomeric material is configured to provide an interference fit with the proximal angled opening of the cannula.

9. The apparatus of claim 1, wherein the apparatus further comprises a hollow cannula, wherein the cannula comprises an annular flange with a proximal angled opening, wherein the exterior tapered surface comprises an elastomeric material, wherein the elastomeric material is configured to provide an interference fit with the outer perimeter of the annular flange of the cannula.

10. The apparatus of claim 1, further comprising an elastomeric material overmolded around the trocar roof.

11. The apparatus of claim 1, further comprising an elastomeric material overmolded around the exterior tapered surface, wherein the apparatus further comprises a hollow cannula, wherein the cannula comprises an annular flange, wherein the elastomeric material is configured for interference with the outer perimeter of the annular flange of the cannula.

12. The apparatus of claim 1, further comprising an o-ring configured to complement the surface of the trocar roof.

13. The apparatus of claim 1, wherein the cannula further comprises a proximal angled opening, wherein the proximal angled opening of the cannula comprises threading, wherein the interior tapered surface further comprises threading configured to complement threading of the proximal angled opening of the cannula.

14. The apparatus of claim 1, wherein the apparatus is formed entirely out of rigid material.

15. The apparatus of claim 1, wherein the apparatus further comprises a seal assembly with external threading, wherein the seal assembly housing further comprises internal threading configured to complement the external threading of the seal assembly such that at least a portion of the seal assembly is configured to threadably fit in the seal assembly housing.

16. The apparatus of claim 15, wherein the apparatus further comprises a hollow cannula, wherein the cannula comprises an annular flange with a proximal angled opening, wherein the proximal angled opening of the cannula comprises internal threading, wherein the interior tapered surface further comprises external threading configured to complement the internal threading of the proximal opening of the cannula.

17. The apparatus of claim 15, wherein the apparatus further comprises a hollow cannula, wherein the cannula comprises an annular flange, wherein the outer perimeter of the annular flange comprises external threading, wherein the exterior tapered surface further comprises internal threading configured to complement the external threading of the outer perimeter of the annular flange of the cannula.

18. An apparatus comprising:
(a) a cannula, wherein the cannula comprises an exterior annular flange with a proximal angled opening;
(b) a seal assembly, wherein the seal assembly has a proximal end and a distal end; and
(c) an adaptor comprising:
  (i) a channel, wherein the channel comprises a proximal end and a distal end, wherein the proximal end of the channel is in fluid communication with the distal end of the seal assembly, wherein the distal end of the channel is in fluid communication with the proximal angled opening of the cannula,
  (ii) a seal assembly housing configured to receive a portion of the seal assembly, wherein seal assembly housing comprises a proximal end and a distal end, wherein the proximal end comprises an annular surface, wherein the annular surface is configured to provide a seal between the adaptor and the seal assembly,
  (iii) an interior tapered surface encompassing at least the distal end of the channel, wherein the interior tapered surface comprises a proximal end and a distal end, wherein the proximal end has a larger perimeter than the distal end, wherein the interior tapered surface is configured for insertion into the proximal angled opening of the cannula, and
  (iv) an exterior tapered surface encompassing at least the proximal end of the exterior annular flange.

19. An apparatus comprising:
(a) a cannula, wherein the cannula comprises an annular flange extending about a proximal opening, wherein the proximal opening is defined by a sidewall;
(b) a seal assembly, wherein the seal assembly defines a passageway configured to receive a surgical instrument, wherein the seal assembly further comprises at least one sealing member configured to seal against a surgical instrument disposed in the passageway; and
(c) an adaptor configured to couple the cannula with the seal assembly, wherein the adaptor comprises:
  (i) a first cannula mounting feature positioned in the proximal opening, wherein the cannula mounting feature is configured to seal against the sidewall defining the proximal opening, wherein the cannula mounting feature is further configured to provide a path for insertion of an instrument from the seal passageway of the seal assembly to the proximal opening of the cannula,
  (ii) a second cannula mounting feature positioned about the annular flange, and
  (iii) a seal assembly housing configured to house the seal assembly above the first cannula mounting feature and the second cannula mounting feature.

* * * * *